US005401748A

United States Patent [19]

Sauer et al.

[11] Patent Number: 5,401,748

[45] Date of Patent: Mar. 28, 1995

[54] 2,14-DISUBSTITUTED ERGOLINES, THEIR PRODUCTION AND USE IN PHARMACEUTICAL COMPOSITIONS

[75] Inventors: Gerhard Sauer; Helmut Wachtel; Peter A. Löschmann, all of Berlin, Germany

[73] Assignee: Schering Aktiengesellschaft, Berlin and Bergkamen, Germany

[21] Appl. No.: 988,964

[22] PCT Filed: Jul. 9, 1992

[86] PCT No.: PCT/DE92/00569

§ 371 Date: Mar. 12, 1993

§ 102(e) Date: Mar. 12, 1993

[87] PCT Pub. No.: WO93/01185

PCT Pub. Date: Jan. 21, 1993

[30] Foreign Application Priority Data

Jul. 12, 1991 [DE] Germany ........................ 41 23 587.8

[51] Int. Cl.[6] ..................... C07D 457/12; A61K 31/48

[52] U.S. Cl. ...................................... 514/288; 546/67; 546/68

[58] Field of Search ..................... 546/67, 68; 514/288

[56] References Cited

U.S. PATENT DOCUMENTS

| | | | |
|---|---|---|---|
| 4,731,367 | 3/1988 | Sauer et al. | 514/288 |
| 4,847,262 | 7/1989 | Sauer et al. | 514/288 |
| 4,863,929 | 9/1989 | Sauer et al. | 514/288 |
| 5,037,832 | 8/1991 | Brumby et al. | 514/288 |

*Primary Examiner*—Johann Richter
*Assistant Examiner*—John Peabody
*Attorney, Agent, or Firm*—Millen, White, Zelano, & Branigan

[57] ABSTRACT 2,14-Disubstituted ergolines of formula I

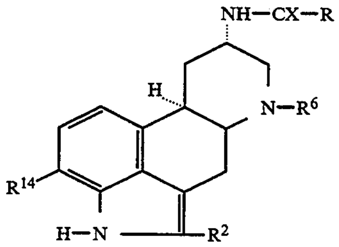

I in which R, $R^2$, $R^6$, $R^{14}$ and X have the meaning named in the application, as well as their production and use in pharmaceutical agents, are described.

4 Claims, No Drawings

2,14-DISUBSTITUTED ERGOLINES, THEIR PRODUCTION AND USE IN PHARMACEUTICAL COMPOSITIONS

The invention relates to new 2,14-disubstituted ergolines, their production and use in pharmaceutical agents.

2-Substituted ergolines, which exhibit affinity for central dopamine receptors and have $\alpha_2$-receptor-blocking action, are known from EP-A-160 842. The new 2,14-disubstituted ergolines show a good or increased dopaminergic agonist activity and simultaneously an improvement of the metabolic stability and thus an increase of action.

The invention relates to compounds of formula I

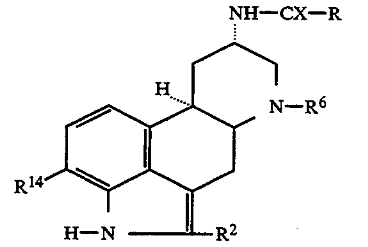

I in which $R^2$ is $C_{1-4}$ alkyl, $R^6$ is $C_{1-6}$ alkyl, $C_{3-6}$ alkenyl or $C_{3-5}$ cycloalkyl-$C_{1-2}$ alkyl, X is oxygen or sulfur, $R^{14}$ is $C_{1-6}$ alkyl, —CO—$R^3$ or —$CR^4R^5$OH and $R^3$, $R^4$ and $R^5$ each mean hydrogen or $C_{1-5}$ alkyl, R means $N(C_2H_5)_2$, $SCH_3$, hydrogen or optionally substituted $C_{1-7}$ alkyl as well as their acid addition salts or isomers.

The physiologically compatible acid addition salts are derived from the known inorganic and organic acids, such as, for example, hydrochloric acid, sulfuric acid, hydrobromic acid, citric acid, maleic acid, fumaric acid, tartaric acid, i.a.

By alkyl is understood respectively a straight-chain or branched alkyl radical, such as, for example, methyl, ethyl, n-propyl, isopropyl, n-butyl, isobutyl, sec-butyl, tert-butyl, pentyl, hexyl, 2,2-dimethylpropyl, 2-methylbutyl, isopentyl, heptyl, isoheptyl.

If $R^6$ means an alkenyl radical, the latter can be straight-chain or branched and contains preferably only one double bond, and the double bond cannot be adjacent to the nitrogen atom. As alkenyl radicals, for example, 2-propenyl, 1-methyl-2-propenyl, 2-butenyl, methallyl are suitable.

If $R^6$ means a cycloalkyl-alkyl group, radicals with up to 5 carbon atoms, for example, cyclopropylmethyl, cyclopropylethyl and cyclobutylmethyl, are preferred.

As alkyl radicals R, methyl, ethyl, isopropyl, tert-butyl, ethyl-methyl-propyl are especially suitable. As substituents of the alkyl radicals, methoxy, acetoxy, halogen and especially fluorine are suitable.

The compounds of formula I can occur, if a chiral center is present, as diastereomers and as their mixtures. The isomers and mixtures of isomers are also encompassed by this invention.

The compounds of formula I as well as their acid addition salts are usable as pharmaceutical agents because of their agonistic affinity for central dopamine receptors.

The compounds are suitable because of their agonistic activity on central dopamine receptors especially for treatment of Parkinson's disease and hyperprolactinemia.

The dopaminergic agonistic effect is determined, for example, with the help of method, described by Horowski and Wachtel, of the registration of stereotypies by observation of behavior (Eur. J. Pharmacol. 36: 373-383, 1976):

Immediately after intraperitoneal test substance or vehicle administration, female Wistar rats (90-110 g) are placed individually in observation cages made from transparent acrylic glass (25×19×13.5 cm). At 30, 60, 120, 240, 360 and 480 minutes after pretreatment, the presence of behavior stereotypies (chewing, licking, gnawing) is registered by observation of the animals for 2 minutes (i.e., of 30th-32nd, 60th-62nd, 120th-122nd minutes, etc.). Animals which during the 2-minute observation period show continuous chewing, licking and gnawing movements (longer than 30 seconds) are considered stereotypic.

The number of animals per treatment group with behavior stereotypies is determined during the various observation times. The different treatment groups consist of n=8 animals each. Average effective dose ($ED_{50}$) is determined with 95% range of confidence for the various observation times with the help of probit analysis. The results are represented in table 1.

The compounds according to the invention are introduced in a dose of 0,001 to 10 mg of active substance in a physiologically compatible vehicle. The use of the compounds according to the invention takes place in a dose of 0.00001 to 0.1 mg/kg/day, preferably 0.001 to 0.1 mg/kg/day analogously to the known agent bromocryptine.

TABLE 1

Time behavior of the stereotypy-triggering activity of 2,14-disubstituted ergolines in rats after one-time i.p. -pretreatment. Effective doses ($ED_{50}$) with 95% range of confidence were determined with the help of the probit analysis.

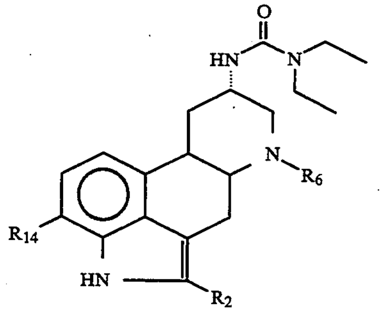

| $R_2$ | $R_6$ | $R_{14}$ | n | time [min] | Activity $ED_{50}$[mg/kg] | 95% range of confidence |
|---|---|---|---|---|---|---|
| $CH_3$ | $CH_2CH_2CH_3$ | $CH_3$ | 8 | 30 | 0.055 | 0.017-0.110 |
| $CH_3$ | $CH_2CH_2CH_3$ | $CH_3$ | 8 | 60 | <0.025 | — |
| $CH_3$ | $CH_2CH_2CH_3$ | $CH_3$ | 8 | 120 | <0.025 | — |
| $CH_3$ | $CH_2CH_2CH_3$ | $CH_3$ | 8 | 240 | <0.025 | — |
| $CH_3$ | $CH_2CH_2CH_3$ | $CH_3$ | 8 | 360 | 0.071 | 0.039-0.130 |
| $CH_3$ | $CH_2CH_2CH_3$ | $CH_3$ | 8 | 480 | 0.072 | 0.039-0.130 |

At 30, 60, 120, 240, 360 and 480 minutes after i.p. pretreatment with test substance or vehicle, the presence of behavior stereotypies in rats (chewing, licking, gnawing) was determined by observation for 2 minutes (i.e., of 30th-32nd, 60th-62nd, 120th-122nd minutes, etc.). Animals which showed chewing, licking or gnawing movements during the 2-minute interval were considered stereotyped (method according to Horowski, R. and Wachtel, H., Eur. J. Pharmacol. 36: 373-383, 1976), n=number of animals used per treatment group.

To use the compounds according to the invention as pharmaceutical agents, the compounds are brought into the form of a pharmaceutical preparation, which, in addition to the active ingredient for enteral or parenteral administration, contains suitable pharmaceutical, organic or inorganic inert vehicles, such as, for example, water, gelatin, gum arabic, lactose, starch, magnesium stearate, talc, vegetable oils, polyalkylene glycols, etc. The pharmaceutical preparations can be present in solid form, for example, as tablets, coated tablets, suppositories, capsules, or in liquid form, for example, as solutions, suspensions or emulsions. Optionally, they also contain auxiliary agents, such as preservatives, stabilizers, wetting agents or emulsifiers, salts to change the osmotic pressure or buffers.

The production of the compounds of formula I according to the invention can be performed according to methods known in the art.

For example, compounds of formula I are attained, by compounds of formula II

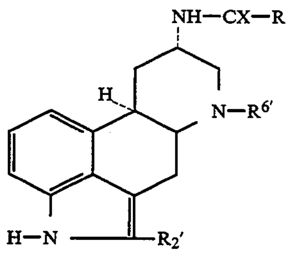

II in which R and X have the above-named meaning, $R^{2'}$ means morpholinomethyl or $C_{1-4}$ alkyl, $R^{6'}$ means cyano or has the above-named meaning of $R^6$, being reacted in the presence of an acid with an acylation agent and if $R^{2'}$ means morpholinomethyl, optionally being reduced after quaternarization to $R^2=CH_3$ or if $R^{6'}$ means cyano, being reacted to compounds with $R^6$ in the above meaning and optionally then α) compounds with $R^{14}$=—CO—$R^3$ in the above meaning being reduced to compounds with $R^{14}$=—$CR^4R^5OH$ and the latter optionally being reduced to compounds with $R^{14}=C_{1-6}$ alkyl or β) urea being converted to thiourea or γ) the isomers being separated or the acid addition salts being formed.

The electrophilic substitution in 14-position is performed in the presence of an acid at temperatures of 0° C. to 20° C. and is generally completed after 1 to 24 hours.

Inorganic acids, such as phosphoric acid, sulfuric acid, organic acids, such as trifluoroacetic acid, methanesulfonic acid, acetic acid, and Lewis acids, such as aluminum chloride, titanium chloride, dimethylaluminum chloride, tin(IV) chloride, boron fluoride, i.a., can be used as acids, and the organic acid can be used as solvent or inert aprotic solvents, such as chlorinated hydrocarbons, such as dichloromethane, chloroform, tetrachloroethane or nitrobenzene, are added.

Suitable acylation agents are, for example: acyl chlorides, such as acetyl chloride, propionyl chloride; dichloromethyl alkyl ether, chloroformic acid alkyl ester; acetic anhydride, i.a.

Compounds of formula I with $R^{14}$ meaning a —$COR^3$ group can be reduced to the alcohol according to the usual processes, such as, for example, with lithium aluminum hydride or lithiumtri-tertbutoxyalanate in an aprotic solvent, such as cyclic or acyclic ethers, for example, tetrahydrofuran, dioxane, diethyl ether. Tertiary carbinols can also be produced as substituents $R^{14}$ by Grignardation or lithium alkylation. The Grignardation can take place with the usual Grignard reagents, such as alkyl magnesium halides in an aprotic solvent, such as cyclic and acyclic ethers, at temperatures of −70° C. to 20° C. The reaction with alkyl lithium takes place under analogous conditions.

The reduction of the alcohols to 14-alkyl derivatives can take place, for example, by reaction with $NaBH_4$ in acetic acid or by reduction with lithium in ammonia.

To introduce the 14-alkyl group, it can be advantageous, before the reduction, to esterify the hydroxy group with acids, such as pivalic acid, acetic acid, benzoic acid.

To produce the 2-methyl derivative, the morpholinomethyl group can optionally be reduced after conversion to its quarternary salt, for example, with methyl iodide, according to the process described in EP-A-351 352, in polar solvents with $NaBH_4$. The reduction can take place before or after introduction of the substituents in 14- or 6-position.

The introduction of the substituents in 6-position can take place, for example, according to A. Cerny et al. Coll. Czech. Chem. Comm. 49, 2828 (1984) or according to the process described in EP-21 206, by the 6-H compound being produced from the 6-cyano compound, for example, by reduction with zinc in glacial acetic acid, the 6-H compound being reacted with $R^6$ halides (bromides, chlorides, iodides) optionally in the presence of bases such as DBU, alkali hydroxides or alkali carbonates.

The conversion of the urea derivatives to the thioureas can take place, for example, according to the process described in EP-A-217730 by reaction with phosphorus oxychloride and a thiolation agent.

The mixtures of isomers can be separated according to the usual methods, such as, for example, crystallization, chromatography or salt formation in the diastereomers.

The compounds of formula I are isolated either as free bases or in the form of their physiologically compatible acid addition salts.

For the formation of salts, a compound of formula I is dissolved, for example, in a little methanol or methylene chloride and mixed with a concentrated solution of the desired acid.

The production of the initial compounds is described, for example, in WO 90/13550.

In so far as the production of the initial compounds is not described, they are known or can be produced analogously to known compounds or to processes described here.

The following examples are to explain the process according to the invention.

Example 1

8α-(3,3-Diethylureido)-2-methyl-6-propyl-ergoline-14-carbaldehyde 15.96 g of 1,1-diethyl-3-(2-methyl-6-propyl-8α-ergolinyl)-urea (41.7 mmol) is dissolved in 2 liters of dichloromethane under argon and 25 g of aluminum chloride is added. 40 ml of dichloromethylmethyl ether is instilled and it is stirred for 30 minutes at room temperature. Then, the mixture is cooled in an ice bath, first with ice, then mixed with a solution of 28 g of tartaric acid in 500 ml of water and stirred for 30 minutes. It is made alkaline with 100 ml of a 25% ammonia solution, stirred for 45 minutes, extracted with dichloromethane and evaporated after drying with sodium sulfate. The residue of 18.7 g is dissolved in 200 ml of methanol, mixed with 8 ml of a 40% solution of trimethyl-benzyl-ammonium hydroxide in methanol (triton B) and stirred for 2 hours at room temperature. Then, it is diluted with saturated common salt solution, shaken out with dichloromethane and after drying, the organic phase is evaporated to dryness. The residue is chromatographed on silica gel with hexane/acetone, and 8.8 g of fraction 1 and 2.27 g of fraction 2, basically the 13-aldehyde, are isolated. Fraction 1 is dissolved in methanol and the initial material is crystallized (6.68 g). The mother liquor is again chromatographed on silica gel, this time with dichloromethane/methanol, and 180 mg of the 14-carbaldehyde is isolated (1.1% of theory).

$[\alpha]_D=+2°$ (0.1% in chloroform)

Analogously, there was produced:

8α-(3,3-Diethylureido)-2-(N-morpholinomethyl)-6-propyl-ergoline-14-carbaldehyde, yield 25%, $[\alpha]_D=+13°$ (0.5% in chloroform)

Example 2

3-(14-Acetyl-2-methyl-6-propyl-8α-ergolinyl)-1,1-diethylurea 48 g of aluminum chloride (360 mmol) is suspended in 1.4 liters of dichloromethane and mixed at room temperature with 26 ml of acetyl chloride (360 mmol). After 15 minutes of stirring, an almost clear solution has developed, which is poured under argon into the solution of 15 g of 1,1-diethyl-3-(2-methyl-6-propyl-8α-ergolinyl)-urea (40 mmol) in 600 ml of dichloromethane and stirred for 30 minutes. Then, the solution is cooled in the ice bath, mixed with ice and a solution of 56 g of tartaric acid in 1 liter of water and, after another 30 minutes of stirring, made alkaline with 200 ml of 25% ammonia. After 45 minutes of stirring, the phases are separated and the aqueous phase is shaken out with dichloromethane. The organic phases are dried with sodium sulfate and concentrated by evaporation, the residue is chromatographed on silica gel with dichloromethane/methanol. In this way, a nonpolar fraction is separated, which is 200 mg of the 14-acetyl compound (1% of theory), the main product forms the 13-acetyl compound (13.9 g, 82% of theory), $[\alpha]_D=-3.5°$ (0.5% in pyridine)

In an analogous way, there were produced:

3-(14-Acetyl-2,6-dimethyl-8α-ergolinyl)-1,1-diethylurea, yield 3.6%, $[\alpha]_D=9°$ (0.1% in chloroform)

3-(14-acetyl-6-methyl-2-(N-morpholinomethyl)-8α-ergolinyl)-1,1-diethylurea, yield 32%, $[\alpha]_D=+11°$ (0.5% in chloroform)

3-(14-acetyl-6-cyano-2-(N-morpholinomethyl)-8α-ergolinyl)-1,1-diethylurea, yield 27%, $[\alpha]_D=74°$ (0.5% in pyridine)

Example 3

3-(14-Ethyl-2-methyl-6-propyl-8α-ergolinyl)-1,1-diethylurea 531 mg of 3-(14-acetyl-2-methyl-6-propyl-8α-ergolinyl)-1,1-diethylurea (1.37 mmol) is dissolved in 75 ml of anhydrous tetrahydrofuran, 300 mg of lithium aluminum hydride is added and heated for 30 minutes to 60° C. It is allowed to cool, 0.3 ml of water, 0.3 ml of 4N sodium hydroxide solution and 0.9 ml of water are added in succession with vigorous stirring. After one hour of stirring, it is filtered, the filtrate is concentrated by evaporation and the residue is chromatographed on silica gel with hexane/acetone. 317 mg of the 14-hydroxyethyl compound, which is dissolved in 3 ml of pyridine and acetylated with 0.6 ml of acetyl chloride, is isolated. After 10 minutes, it is mixed with ice, allowed to stand for 30 minutes and extracted with dichloromethane. After complete evaporation of the solvent, the residue is dissolved in 5 ml of tetrahydrofuran, this solution is added at −70° C. to 20 ml of anhydrous ammonia and reduced with 70 mg of lithium. After 30 minutes of stirring, it is mixed with ammonium chloride until the disappearance of the blue coloring, then carefully with 5 ml of water and the ammonia is evaporated off. With ice cooling and addition of water, it is crystallized, yield 177 mg (yield 32% of theory), $[\alpha]_D=-0.7°$ (0.5% in chloroform).

In an analogous way, there are produced:

3-(2,14-Dimethyl-6-propyl-8α-ergolinyl)-1,1-diethylurea, yield 66% of theory, $[\alpha]_D=+7°$ (0.1% in chloroform)

1,1-diethyl-3-(2,6-dimethyl-14-ethyl-8α-ergolinyl)-urea, yield 47% of theory, $[\alpha]_D=+4°$ (0.1% in chloroform)

Example 4

3-(14-Ethyl-2-methyl-6-propyl-8α-ergolinyl)-1,1-diethylurea 492 mg of 3-(14-acetyl-6-cyano-2-(N-morpholinomethyl)-8α-ergolinyl)-1,1-diethylurea (1 mmol) is dissolved in 20 ml of tetrahydrofuran, 0.4 ml of methyl iodide (6.5 mmol) is added and stirred for 22 hours at room temperature. The mixture is cooled in an ice bath, mixed with 10 ml of isopropyl ether and the precipitate is suctioned off. The quarternary salt is reduced as described in the preceding example (substance suspended in tetrahydrofuran), the crude product is dissolved in 50 ml of nitromethane, mixed with 1 g of potassium carbonate, 150 mg of tetrabutylammonium hydrogen sulfate and 0.7 ml of propyl iodide and stirred overnight at room temperature. The mixture is taken up in water, extracted with dichloromethane, the organic phase is dried with sodium sulfate and concentrated by evaporation. After crystallization from ethyl acetate/diisopropyl ether, 184 mg (45% of theory), identical with the above-described compound, is obtained.

Example 5

Starting from said 8α-amides, the following derivatives are produced in the reaction sequences described in the above examples or their combination and optionally converted to the thioamides:

N-(2,14-Dimethyl-6-n-propyl-8α-ergolinyl)-methoxyacetamide

N-(2,14-dimethyl-6-n-propyl-8α-ergolinyl)-trifluoroacetamide

N-(2,14-dimethyl-6-n-propyl-8α-ergolinyl)-ethyl-methyl-butyric acid amide

N-(2,14-dimethyl-6-n-propyl-8α-ergolinyl)-thioformamide

N-(2,14-dimethyl-6-n-propyl-8α-ergolinyl)-dithiocarbamic acid methyl ester

We claim:

1. A compound of formula I

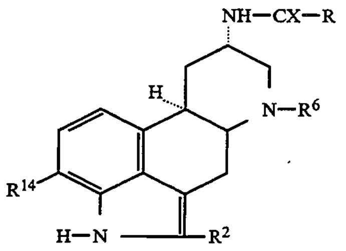

I wherein $R^2$ is $C_{1-4}$ alkyl, $R^6$ is $C_{1-6}$ alkyl, $C_{3-6}$ alkenyl or $C_{3-5}$ cycloalkyl-$C_{1-2}$ alkyl, X is oxygen or sulfur, $R^{14}$ is $C_{1-6}$ alkyl, —CO—$R^3$ pr $CR^4R^5OH$ and $R^3$, $R^4$ and $R^5$ each are hydrogen or $C_{1-5}$ alkyl, and R is $N(C_2H_5)_2$, $SCH_3$, hydrogen or $C_{1-7}$ alkyl optionally substituted by methoxy, acetoxy, or halogen, or a diastereomer or acid addition salt thereof.

2. The compound selected from the group consisting of

8α-(3,3-Diethylureido)-2-methyl-6-propyl-ergoline-14-carbaldehyde, 3-(14-ethyl-2-methyl-6-propyl-8α-ergolinyl)-1,1-diethylurea, 3-(2,14-dimethyl-6-propyl-8α-ergolinyl)-1,1-diethylurea, 1,1-diethyl-3-(2,6-dimethyl-14-ethyl-8α-ergolinyl)-urea, 3-(14-ethyl-2-methyl-6-propyl-8α-ergolinyl)-1,1-diethylurea, N-(2,14-dimethyl-6-n-propyl-8α-ergolinyl)-methoxyacetamide, N-(2,14-dimethyl-6-n-propyl-8α-ergolinyl)-trifluoroacetamide N-(2,14-dimethyl-6-n-propyl-8α-ergolinyl)-ethylmethylbutyric acid amide, N-(2,14-dimethyl-6-n-propyl-8α-ergolinyl)-thioformamide and N-(2,14-dimethyl-6-n-propyl-8α-ergolinyl)-dithiocarbamic acid methyl ester.

3. A pharmaceutical composition comprising a compound of claim 1, and a pharmaceutically acceptable auxiliary agent or inert vehicle.

4. A process for the production of a compound of claim 1, comprising reacting a compound of formula II

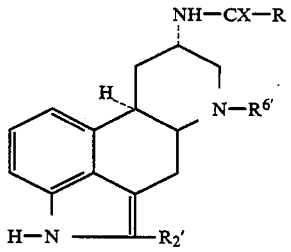

II wherein

X and R have the above meaning, and $R^{2'}$ has the above meaning of $R^2$ or is morpholinomethyl, and $R^{6'}$ independently, has the above meaning of $R^6$ or is cyano, in the presence of an acid with an acylation agent, and, if $R^{2'}$ is morpholinomethyl, optionally reducing the thus-produced product, after quaternization, to a compound wherein $R^2$ is $CH_3$, or if $R^{6'}$ is cyano, converting the thus produced-product to a compound wherein $R^6$ has the above meaning, and optionally then α) further reducing said compound wherein $R^{14}$ is —CO—$R^3$ having the above meaning to a compound wherein $R^{14}$ is —$CR^4R^5OH$, and the latter is optionally reduced to a compound wherein $R^{14}$ is $C_{1-6}$ alkyl, or β) converting a urea group, if present, to thiourea, or γ) separating diastereomers, if present, or forming an acid addition salt.

* * * * *